United States Patent [19]

Colon et al.

[11] Patent Number: 6,095,202
[45] Date of Patent: Aug. 1, 2000

[54] METHOD AND DEVICE FOR PACKING CAPILLARY COLUMNS

[75] Inventors: Luis A. Colon, Amherst, N.Y.; Adam M. Fermier, Lebanon, N.J.; Gary R. Sagerman, Darien Center, N.Y.

[73] Assignee: Research Foundation State University of New York, Albany, N.Y.

[21] Appl. No.: 09/060,486

[22] Filed: Apr. 15, 1998

Related U.S. Application Data

[60] Provisional application No. 60/044,683, Apr. 18, 1997.

[51] Int. Cl.[7] .................................................. B01D 15/08
[52] U.S. Cl. ............................ 141/34; 141/1; 210/198.2; 210/657
[58] Field of Search ........................ 141/1, 34; 210/198.2, 210/657

[56] References Cited

U.S. PATENT DOCUMENTS

| | | | |
|---|---|---|---|
| 3,315,437 | 4/1967 | Henriksen | 141/34 |
| 3,770,027 | 11/1973 | Guigan | 141/34 |
| 3,935,884 | 2/1976 | Hazelton | 141/80 |
| 3,986,534 | 10/1976 | Schmidt | 141/1 |
| 4,422,941 | 12/1983 | Vaughan, Jr. et al. | 210/657 |
| 4,900,446 | 2/1990 | Anderson | 210/657 |
| 4,985,143 | 1/1991 | Freeman et al. | 210/198.2 |

*Primary Examiner*—J. Casimer Jacyna
*Attorney, Agent, or Firm*—Crossetta & Associates

[57] ABSTRACT

The present invention features a method and apparatus with a rotatable central reservoir and radially extending support arms for packing chromatographic columns at a consistent gradient of particle impact by using centripetal forces to independently accelerate particles comprising a bed material through a filling opening at one end of the column and continuously as they move axially along the length of the column to their packed destination. The method and apparatus are particularly suitable for use in packing capillary columns having an interior diameter of about 500 microns or less.

26 Claims, 8 Drawing Sheets

METHOD AND DEVICE FOR PACKING CAPILLARY COLUMNS

This continuation of application Ser. No. 60/044,683, filed Apr. 18, 1997.

FIELD OF THE INVENTION

This application relates to a novel method and device for packing columns used in chromatographic systems for the separation and/or identification of chemical components of a complex chemical mixture, and has particular application to the packing of capillary columns having an internal diameter of about 500 microns or less.

BACKGROUND OF THE INVENTION

Chromatography is a method of separating complex chemical mixtures wherein individual chemical species of the mixture are distinguished from each other through selective distribution among heterogeneous phases for analytical and/or preparative purposes.

The distribution process is a dynamic process wherein the mixture is passed through a bed of particulate material and species of the mixture, having greater or lesser affinity to the bed material, are distinguished from others by being retained longer or passing through the bed more quickly. A mobile phase is used to carry the species through the column.

The mobile phase can comprise either a gas, liquid or supercritical fluid, thus a chromatographic method is referred to as gas chromatography, liquid chromatography or supercritical fluid chromatography. Separation of the mixture is based upon physical and/or chemical principles of adsorption and partition phenomena and thus the consistency of the bed and the materials comprising the bed control the attainment of repeatable accuracy and sensitivity for separation and/or identification of components.

The bed of a chromatographic apparatus comprises a column of particulate material, through which the mixture is percolated by gravity, electroosmotic flow or various pressures. In liquid chromatography, a contemporary direction is the utilization of high performance systems wherein the complex mixture, in a liquid mobile phase, is pumped at high pressure through a packed column of bed material.

In a typical preparative high performance liquid chromatographic system a mixture of compounds in solution is pumped at high pressure into a packed column of selected bed material. By means of the appropriate selection of bed material and liquid mobile phase, the column retains the components of the mixture to enable the discrete elution and separate collection of distinguished components of the mixture.

Generally, the size of the columns used in chromatography are dependent upon whether the system is gas or liquid and whether the use is for analytical or preparative purposes. Recent high performance liquid chromatographic systems have been developed which utilize analytical semi-preparative processes. Regardless of the size of the column, the overall performance of the column is highly dependent upon the manner by which the column is packed to form the bed and the consistency of the packing within the bed.

Generally, in preparing a packed column, a carefully proportioned slurry is formed comprising the bed material. The slurry is inserted into the column and liquid comprising the slurry is removed from the column to form a bed of particulate material in a packed arrangement. As the internal diameter of a column is decreased, particularly for use in capillary liquid chromatographic apparatus, processes for packing the column have become critical and tedious to enable a tight homogenous distribution of particulate material without voids or particle agglomeration, and comprising a consistent interspacial relationship between packed particles. Thus, there has been difficulties associated with the preparation of packed columns, particularly capillary columns which have an internal diameter of about 500 microns or less. The processes currently being used to pack capillaries are generally viewed as being tedious and having undesirable failure rates due to inconsistent homogeneity of the final packed capillary.

Most methods of packing currently used involve the application of axial compression forces at an end of the column bed to drive the bed material into the column with the subsequently entering material pushing axially against the first entering material to enable packing. One typical such method is a hydraulic packing system wherein a column is fritted at one end to enable passage of liquid but resist passage of particulate bed material. A defined liquid slurry of packing material is pushed into the opposite end of the column under high pressure or by a compression member which essentially constitutes a ram, sized to enter the interior diameter of the column and axially push slurry, trapped between it and the fritted opening of the column, into position within the column. Such elaborate ram driving apparatus, is generally only able to pack a single column at a time, requires significant apparatus modification for changes in column size and diameter and is subject to production of packed columns having significant failure rates for homogeneity of bed material.

Another method conventionally being used, embodies the application of radial compression on a flexible capillary wherein a pliant capillary, and thus the bed material, is radially squeezed by pneumatic or hydraulic pressure to achieve homogeneity. Systems using such method have not solved the problem of homogeneity failure and add the problem of testing the durability of the column.

Still another method which is currently used is an electrophoretic process wherein a voltage is imposed across a capillary, generating an electroosmotic flow that causes the particles to flow toward an attracting polarity and enable packing. Such process is inexpensive in comparison to axial or radial pressure systems but has not been found suitable for use with small particles, such as sub-micron particles which may comprise the bed of small diameter capillaries and is dependent upon the surface chemistry of the particles, thus limiting the materials with which it can be used.

An object of the present invention is to provide a simple and effective method for packing chromatography columns.

A further object of the invention is to provide an effective method to pack capillary columns having an internal diameter of about 500 microns and less.

Another object of the invention is to provide an apparatus for packing chromatographic columns which is convenient to use and has a low rate of packing failures.

A still further object of the invention is to provide packed capillary columns, having an internal diameter of less than about 500 microns, which have improved homogeneity of the packed bed along their axial length.

Still another object of the invention is to provide packed capillary columns, having an internal diameter of less than about 500 microns, which have improved homogeneity of the packed bed along its axial length.

These and other objects of the invention will be apparent from the following description of the invention.

SUMMARY OF THE INVENTION

The present invention comprises a method and apparatus for packing chromatographic columns at a consistent gradient of particle impact throughout the length of the column. Though the method and apparatus are generally applicable to packing any chromatography column, they are particularly suitable for use in packing capillary columns having an interior diameter of less than about 5 mm, and especially suitable for interior diameters of about 500 microns or less, which are particularly desirable for use in a capillary liquid chromatography apparatus.

At its most basic level, the method of the invention essentially comprises imparting a continually accelerating kinetic force to each of the particles intended to comprise a bed material so that during the filling of an elongate column, each particle independently accelerates as it passes through a filling opening at one end of the column and moves axially along the length of the column to its destination within the column, regardless of movement of the liquid comprising the slurry. Thus, each particle comprising the packed bed of the column reaches its packing destination along the column at a defined impact velocity, each impact velocity is closely equivalent to the impact velocity of each adjacent particle similarly arriving at an adjacent destination along the length of the column, and impact velocities at any cross sectional destination along the length of a column are closely equivalent, without requiring liquid movement.

To attain such velocities, the present invention utilizes the effects of centripetal acceleration of a particle along the length of a column. A particle moving in a constant velocity along a circular path must experience a centripetal acceleration toward the center of the circle to maintain its path. The magnitude of impact velocity (a) is a function of its distance (r) from the center of the circle and the angular velocity (w) around the circle, in accord with the relationship $a=Cw^2r$, wherein C represents a constant. Thus, a particle freely moving axially along a constant speed radius rotating about a central axis, will continuously increase in acceleration through both a change in velocity and distance from the central axis. If the particle is comprised in a liquid slurry however, it is inhibited in its axial movement by drag forces and buoyant forces of the liquid, which in turn are governed by particle size, volume and density, and bulk liquid density and viscosity, which is accounted for by the constant C.

In the method of the invention, columns to be packed are arranged as radial spokes, extending from a central reservoir, with a filling opening to the column being arranged proximal the reservoir and a fritted open end of the column, enabled for liquid passage but restrictive of particle passage, being arranged distal therefrom. An appropriate slurry, comprising a desired concentration of sized particulate matter, is provided to the reservoir. The arrangement is rotated and the particle containing slurry is free to move axially from the reservoir through the filling openings of the radially extending columns, continuously increasing in acceleration through a change in velocity as a function of distance from the central axis.

The first passing slurry portion accelerates to the fritted end of the column, with liquid passing through and deposition of particles occurring proximate the fritted end at maximum impact velocities. As packing of particles proceeds from the fritted end, a packing head progresses along the column toward the central axis of the reservoir, the passage of liquid out the fritted end becomes increasingly reduced by the increasing restriction posed by the increasing mass of packed bed of particles in the column. Liquid movement through the capillary slows with a liquid head forming at the interface of slowed liquid movement and newly arriving accelerating slurry. The liquid head progressively moves axially along the column toward the central axis of the reservoir to the filling opening of the column.

With the reduction of movement of the liquid in the column, particle movement in the column toward the packing head is also slowed, a particle moving through the relatively non-moving liquid being inhibited by drag forces and buoyant forces of the liquid. Significantly, though acceleration of a particle is inhibited, particles flowing through the filling opening will still continuously accelerate until impact at the packing head. Thus, each particle arriving at its destination at the packing head of the column, continuously accelerates to the point of impact at the packing head, but with decreasing gradient of impact velocity from a previously impacting particle.

It has been found that with suitable control of slurry components, slurry concentration, rotational speed and particle size parameters that various diameter columns of differing length can be easily and reproducible packed to exacting standards. Such packing method appears to reduce the problem of particle agglomeration in that particles would appear to arrive at their packing destination kinetically independent from adjacent particles and without the significant incident of interparticle collision which characterizes axially compression methods. The kinetically independent arrival of particles, coupled with their random distribution within the liquid slurry and closely equivalent impact velocity at destination, tends to assure that particles tightly pack interstitially through a given cross section of the column. In turn, liquid surrounding and flowing around a particle enables a minimal spacing among the packed particles and enables flow of the liquid, randomly between the particles, out the fritted end.

In a general embodiment of the apparatus of the invention, the reservoir comprises a container having a hollow chamber which has a generally circular inner surface arranged in a plane about perpendicular to a point along a central axis of the chamber. The generally circular inner surface comprises two or more openings to the exterior of the container and means are provided for mounting open filling ends of two or more columns to the container to enable the flow of a slurry from the openings in the generally circular inner surface of the chamber into the columns. The columns are mounted to extend radially outward from the container along axes about generally perpendicular to the central or working axis of the chamber.

In one embodiment of the invention an interior wall surface of the chamber is generally cylindrical. In another embodiment the interior surface of the chamber is spherical or elliptical about the central axis with the openings being arranged at about the greatest perpendicular diameter to the central axis. In a particularly preferred embodiment, the shape of the chamber is frustoconical, with the openings being arranged at about the perimeter of the base of the frustum.

In a further preferred embodiment of the chamber, a mass is provided along the central axis of the reservoir to resist accumulation of particles at the central axis and assure distribution of the slurry toward the opening outlets from the reservoir to the filling openings of the columns.

The present invention is believed to be operable for packing liquid or gas chromatography columns having a wide variety of diameters and lengths and for analytical, preparative and combination uses. The method has particular utility for packing columns having diameters of 500 microns and less and has been found effective in packing columns of 75 microns and less.

Bed materials may vary widely, but contemporary materials are generally a porous or non-porous silica based, Teflon based or other polymeric micro-particulate material of regular and/or irregular shape. The particle size can vary greatly, but with capillary columns is generally about 40 microns or less in diameter and with small grains of material from about 0.05 to about 10 microns being commonly used.

BRIEF DESCRIPTION OF THE DRAWINGS

The nature and mode of operation of the present invention will now be more fully described in the following detailed description taken with the accompanying drawings wherein.

DESCRIPTION OF THE PREFERRED EMBODIMENT

Figure 1:
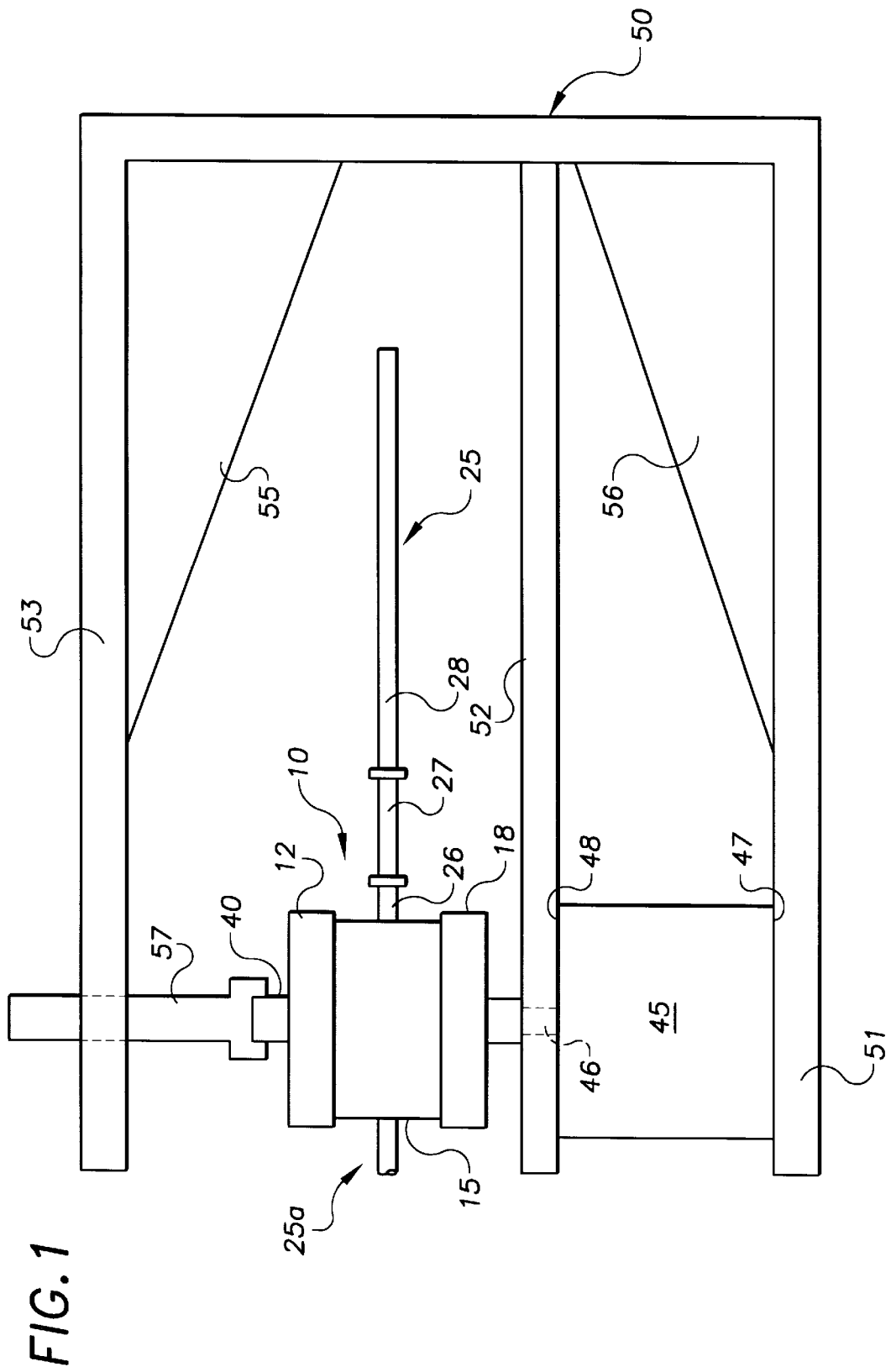
FIG. 1 is a plan view illustration of an assembly of a packing apparatus of the invention.

Referring first to FIG. 1, wherein is illustrated an apparatus of the invention, wherein reservoir assembly 10, comprises upper cap 12, reservoir 15 and lower cap 22, and is mounted to motor shaft 46 of motor 45. Motor shaft 46 is depicted in dotted line as engaging lower cap 20 of reservoir assembly 10. Motor 45 is mounted on its bottom surface 47 to base member 51 of frame 50 and on its top surface 48 to middle support member 52 of frame 50. Upper support member 53 of frame 50 comprises support element 57 for mounting wiper assembly 40. Braces 55 and 56 are arranged as structural support of vertical frame member 54 and upper support member 53 respectively.

The illustrated arrangement enables free rotation of reservoir assembly 10 with the rotation of shaft 46 of motor 45. Capillary support arms 25 and 25a are illustrated as comprising sections 26, 27 and 28 and are mounted to reservoir 15 of reservoir assembly 10.

Figure 2:
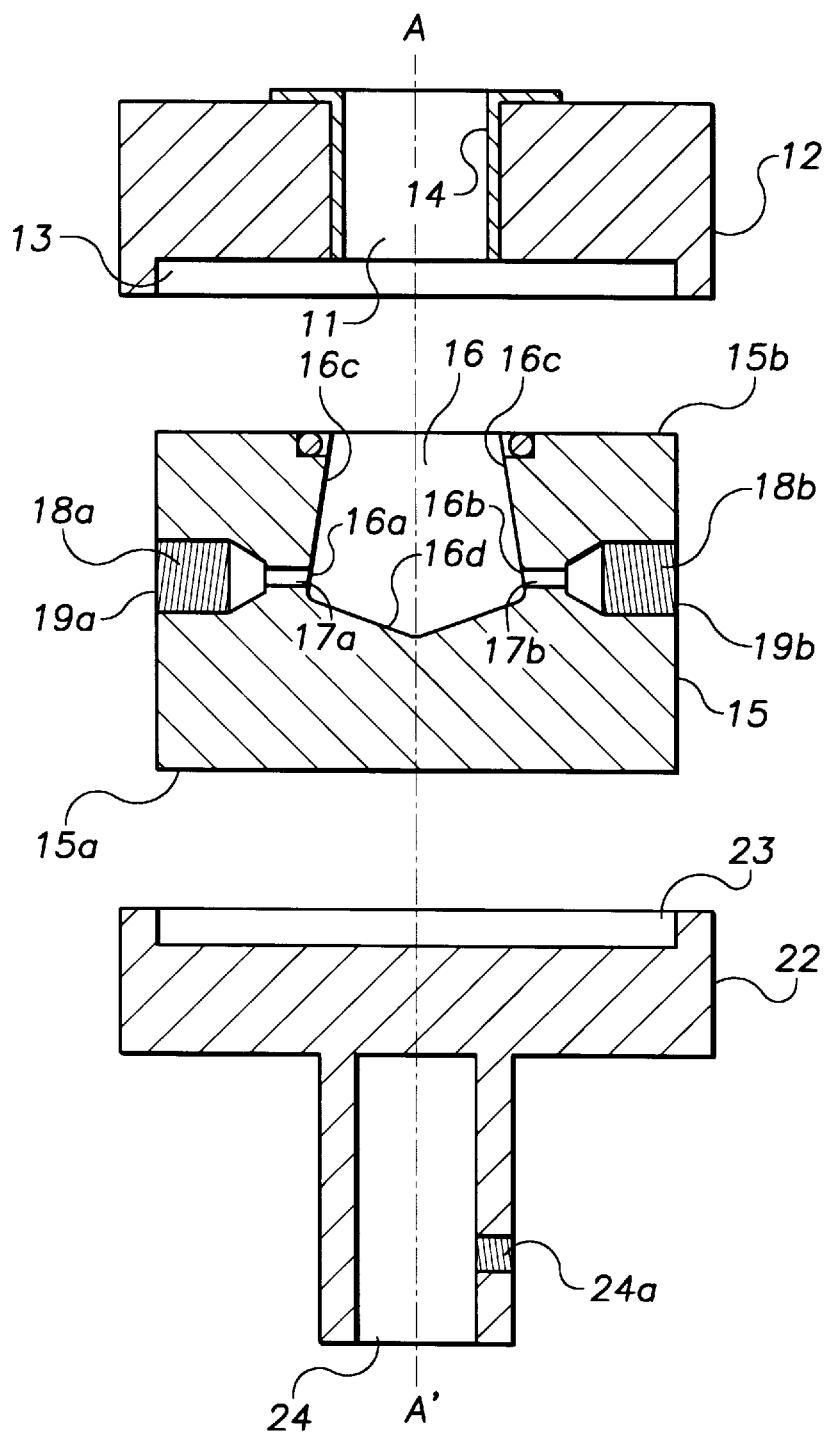
FIG. 2 is an exploded side sectional view of the reservoir illustrated in FIG. 1.
Figure 3:
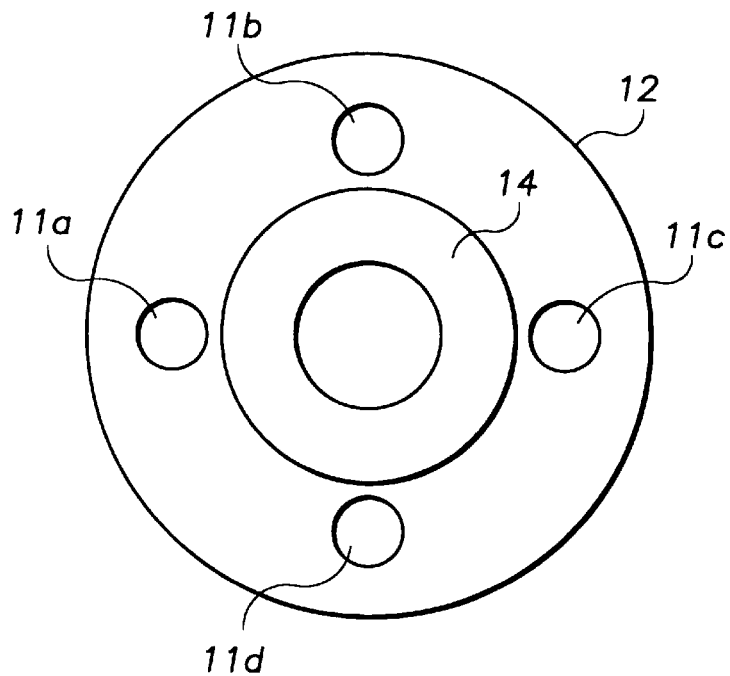
FIG. 3 is a top plan view of the reservoir of FIG. 2.
Figure 4:
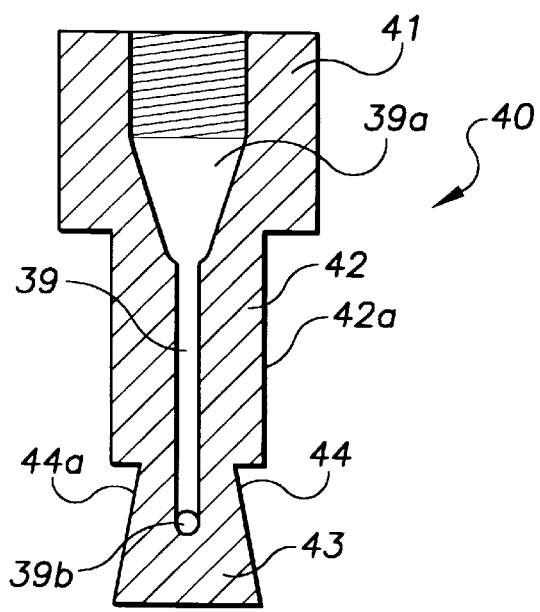
FIG. 4 is a sectional view of a wiper assembly of the reservoir of FIG. 1.

Referring now to FIGS. 2–4, wherein reservoir assembly 10 is illustrated as comprising upper cap 12, reservoir 15 and lower cap 22. Lower cap 22 is illustrated as being cylindrical and comprising a cylindrical end slot 23 sized to matingly engage the bottom end 15a of cylindrical reservoir 15. Deep slot 24 is sized to engage motor shaft 46, and threaded hole 24a is provided to accept a mating threaded screw or the like for engaging and locking the motor shaft within the slot.

Reservoir 15 is illustrated as comprising a central, round reservoir chamber 16, with openings 16a,16b at opposite sides to passageways 17a,17b leading to threaded 18a,18b, support arm mounting openings 19a, 19b. Rounded sidewall 16c of reservoir chamber 16 is illustrated as angled from the reservoir assembly centerline A–A' toward openings 16a, 16b, and base 16d is illustrated as angled from a perpendicular to centerline A–A' toward openings 16a,16b. The angled walls of the chamber are arranged to assist the flow of fluid from the chamber to openings 16a,16b. Top surface 15b of reservoir 15 comprises a circular slot for mounting "O" ring 20, to assure a seal among upper cap 12 and reservoir 15.

Upper cap 12 is illustrated as being cylindrical and comprising a cylindrical end slot 13 sized to matingly engage the top surface 15b of cylindrical reservoir 15. Hole 11 extends through upper cap 12 and is illustrated as comprising bushing 14, which is sized to matingly mount a surface of wiper assembly 40. FIG. 3 illustrates a top plan view of upper cap 12, illustrating bushing 14 and four equidistant holes 11a, 11b, 11c and 11d. Each of these holes is in alignment with mating holes (not shown) in reservoir 15, which in turn are in alignment with mating threaded holes (not shown) in lower cap 22. Bolts (not shown), extend through the upper cap, reservoir and thread into the lower cap for assembly of the reservoir assembly.

FIG. 4 illustrates a wiper assembly operable with the reservoir assembly to churn the slurry in the reservoir during rotation thereof. Therein, wiper assembly 40 is depicted as a cylindrically machined unit, comprising a top end 41, a middle section 42 which comprises a cylindrical exterior wall 42a sized to mate within the interior diameter of bushing 14 of upper cap 12 and lower section 43, comprising a bladed shape having inclined edges 44 and 44a arranged generally parallel to sidewall 16c of reservoir chamber 16. In the illustrated embodiment, a central passageway 39 extends between an opening outlet 39a to reservoir chamber 16 and threaded filling opening 39b, to enable filling of the reservoir chamber. FIG. 1 illustrates wiper assembly 40 as being mounted to support element 57 and is maintained stationary as reservoir assembly 10 rotates.

Figure 5:
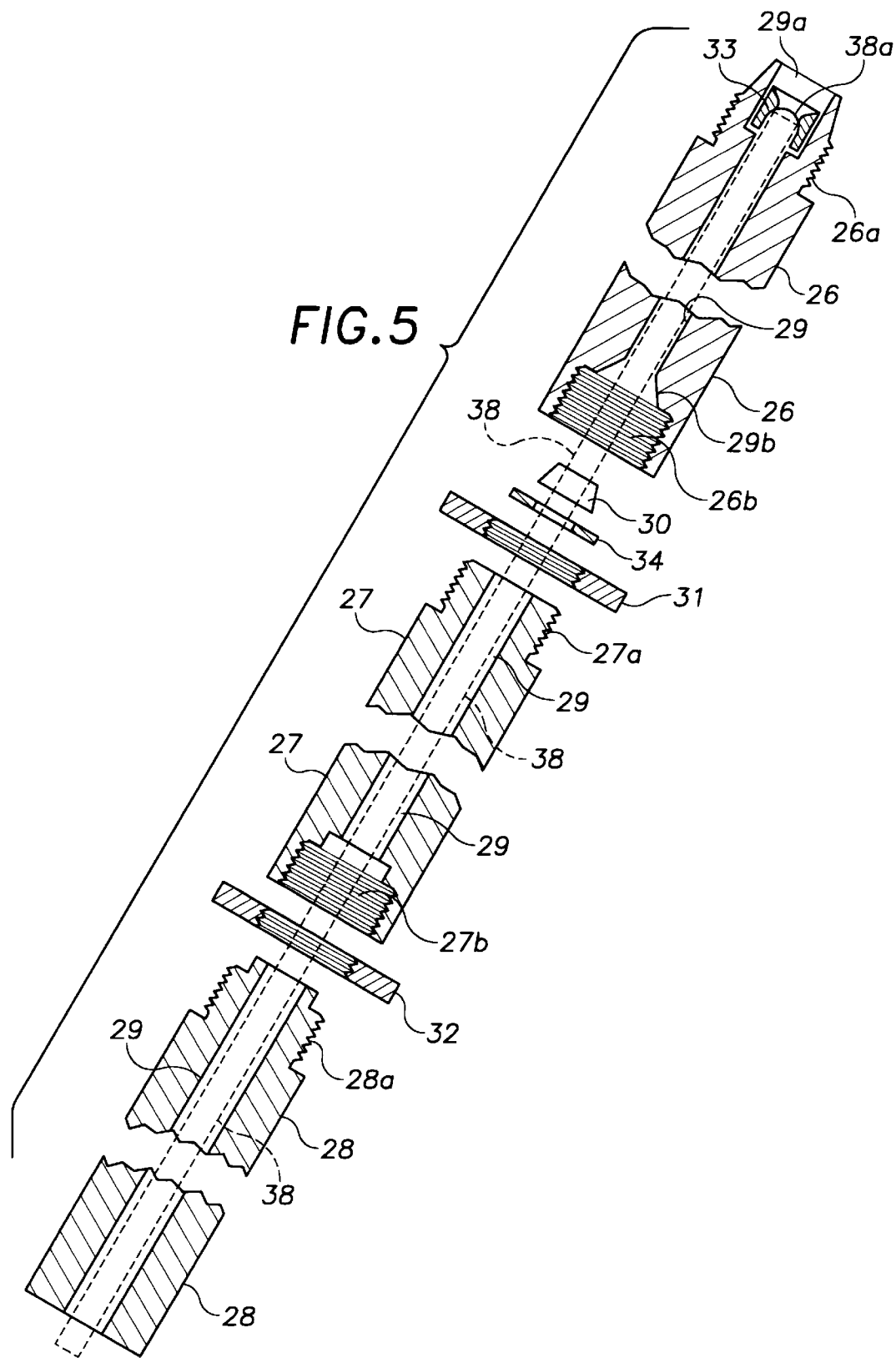
FIG. 5 is an exploded, fragmented sectional view of a capillary support arm of the invention.

FIG. 5 illustrates an arrangement of supporting arm 25, having a central passageway 29, which holds a capillary 38, illustrated in dotted line, to be packed with bed material. End section 26 comprises a male threaded end 26a for threaded mounting in opening 19b of reservoir 15. The central passageway is of increased diameter at 29a, being sized at about the same diameter as passageway 17b of reservoir 15. Capillary end 38a comprises conical funnel 33 which inserts over the capillary and funnels slurry flowing through passageway 17b of reservoir 15 into the filling opening of the capillary at end 38a. At its opposite end, section 26 comprises female threaded receiver 26b, sized to matingly thread with threaded male end 27a of section 27. End 29b of passageway 29 is beveled outwardly to accept a hollow frustoconical ferrule member 30. Ferrule member 30 is comprised of a pliant material through which capillary 38 is inserted. Washer 34 is also arranged around capillary 38, inserts into female threaded receiver 26b, and with the threading of male end 27a into female receiver 26b compresses and holds capillary 38 into place. Nut 31 is provided to lock section 27 to section 26.

At its opposite end, section 27 comprises female threaded receiver 27b, sized to matingly thread with threaded male end 28a of section 28. Central passageway 29 is of the same diameter throughout sections 27 and 28 and is sized to loosely accept capillary 38. Nut 32 is provided to lock section 28 to section 27.

Figure 6:
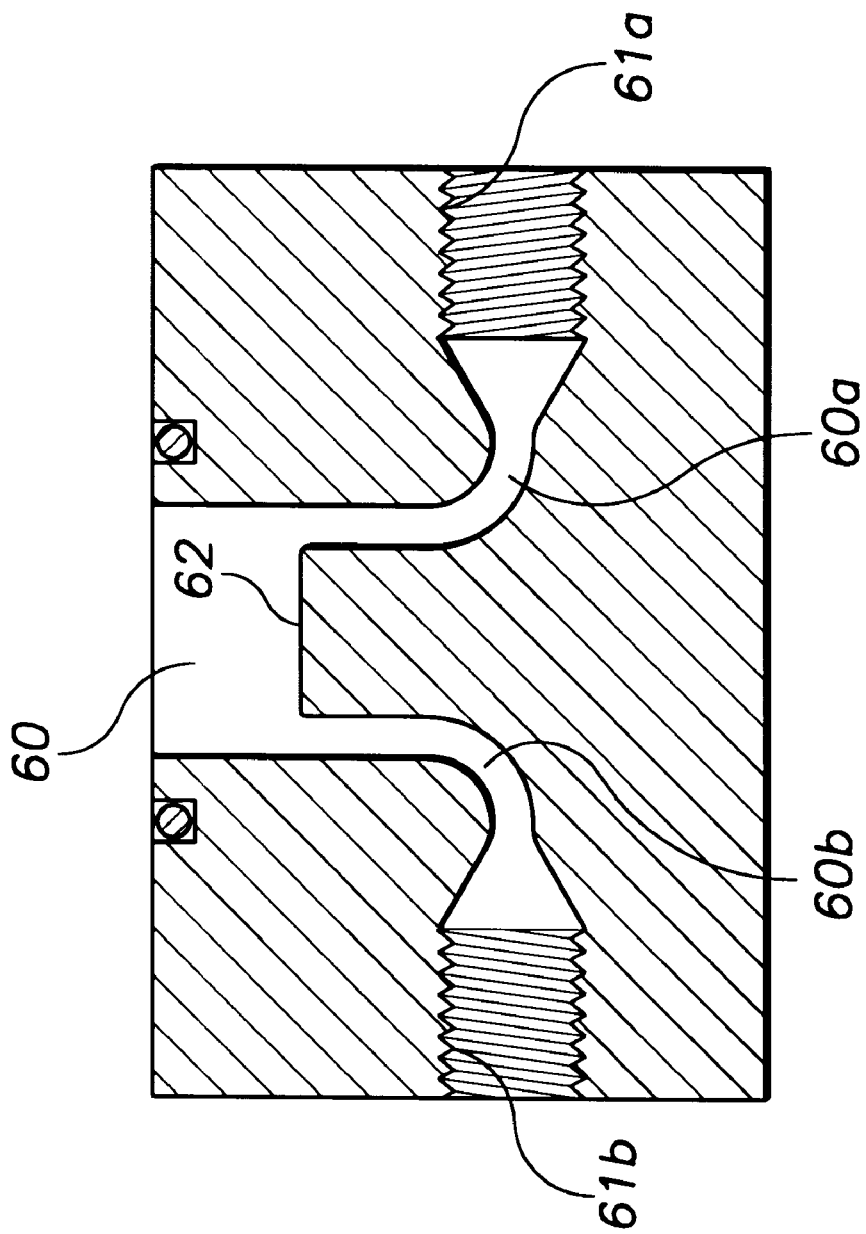
FIG. 6 is a sectional view illustrating another reservoir chamber of the invention.

FIG. 6 illustrates a further reservoir chamber of the invention as comprising a central, frustoconical reservoir chamber 60, with openings 60a,60b at opposite sides leading to threaded support arm mounting openings 61a,61b. A central mass 62 is illustrated as arranged along about the centerline B–B' of the reservoir and the angled sidewall from the centerline is toward openings 60a,60b. In this embodiment, the central mass maintains a slurry from whirlpooling at the centerline and though a wiper assembly may be incorporated therewith, the need for is reduced.

Figure 7:
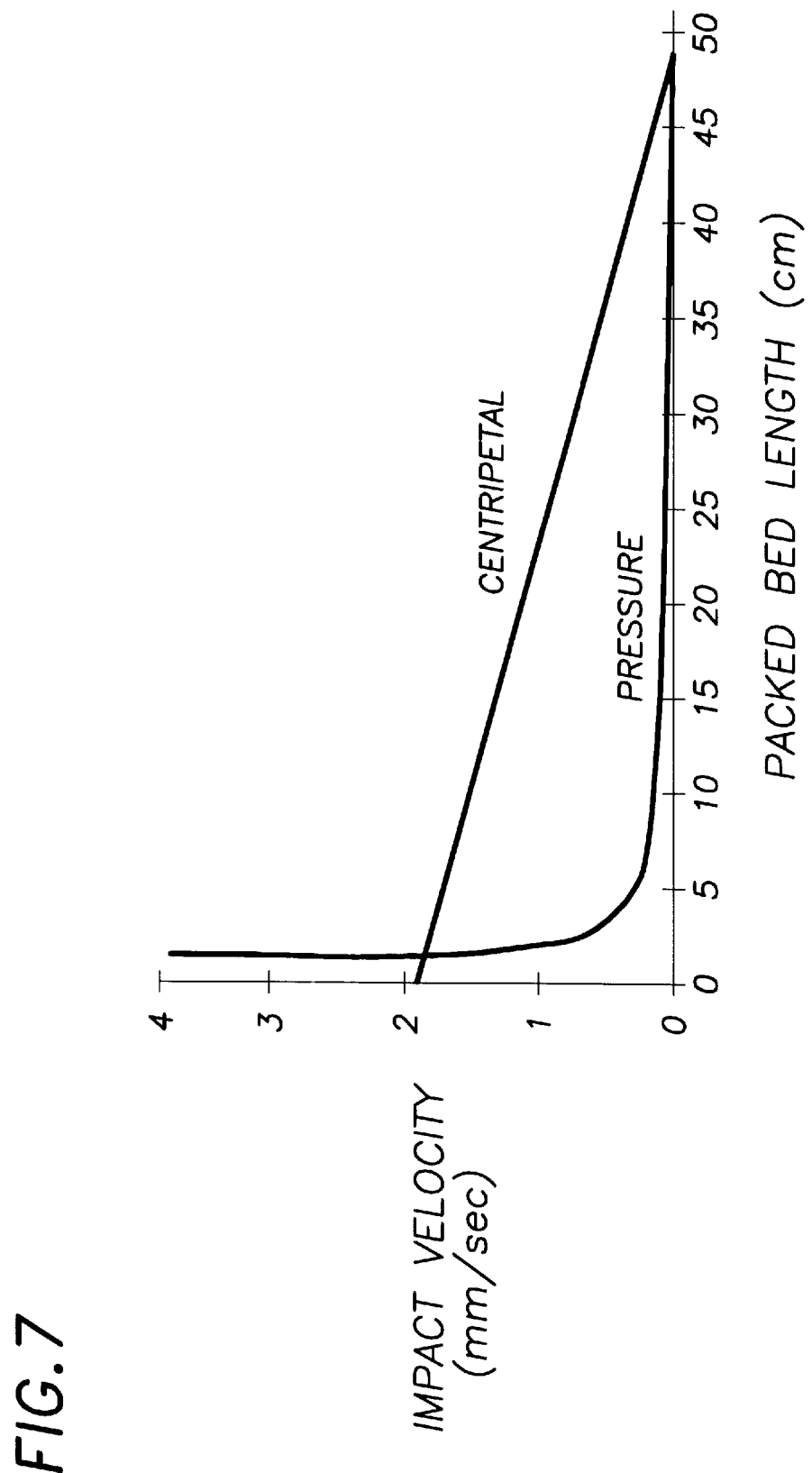
FIG. 7 is a graph depicting comparison of impact velocities along a packed bed formed by axial pressure filling as compared to centripetal force filling.

FIG. 7 comprises a graphic illustration of the difference in packing impact velocity between pressure systems currently used for axially linear packing particulate bed materials in a capillary, and the centripetal method of the present invention. In an axially applied pressure packing system, the slurry solution is pressurized to drive the particles into the column from an open end. In a pressure packing system, the impact velocity of particles packing along the capillary is dependent upon the product of the pressure drop and the square of the particle diameter, divided by the product of the viscosity of the packing slurry, the length of the capillary and the flow resistance factor ($\phi$). In a centripetal packing system the impact velocity of particles along the capillary is dependent upon the product of the difference between the particle density (p) and the fluid density ($p_o$), particle volume (V), particle distance (r) from the center of the circle and the angular velocity (w) squared, divided by three times the product of the viscosity of the packing slurry (''), particle diameter (dp) and $\pi$. FIG. 7 illustrates the impact velocity that a 5 micron particle in methanol at 25° C. will experience by axial pressure (10,000 psi) deposition of the particle as compared to centripetal forces at 1000 rpm, when packing a 50 micron column having a flow resistance factor ($\phi$) of 1000 with a particle density of 0.92 g/mL. As can be seen, the impact velocity when using centripetal force is not decreased as drastic as in the case of pressure packing.

Figure 8:
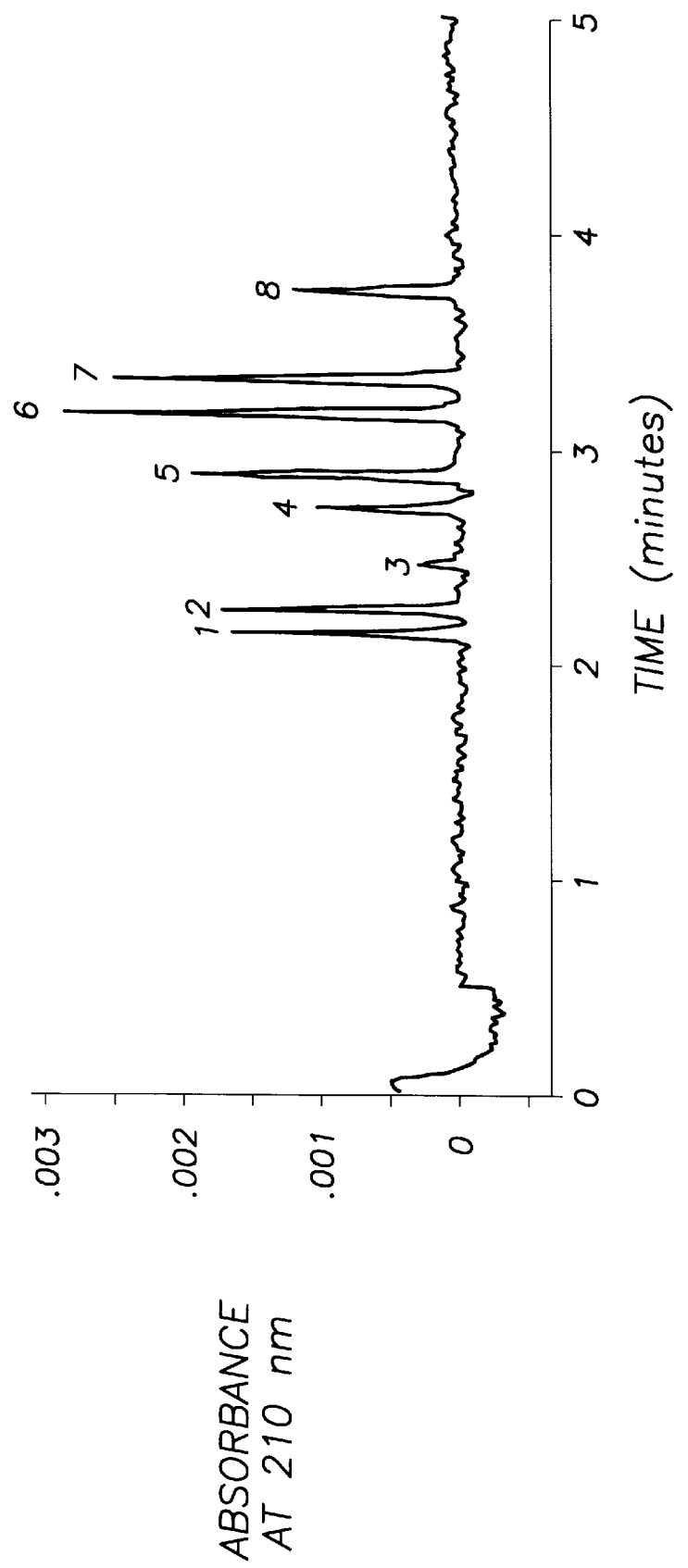
FIG. 8 is a graph depicting species separation in a 30 micron internal diameter capillary column containing a bed packed in accord with the invention.

FIG. 8, comprises a graphic illustration of chemical species separation in a centripetal packed capillary. A packed capillary column, having an internal diameter of 30 microns, overall length of 27 centimeters and bed length of 20 centimeters was prepared by sonicating a 20 mg/ml slurry of $C_{18}$ coated porous silica beads having an average diameter of 3 microns, in methanol for 10 minutes, and filling the capillary centripetally from a central reservoir in a previously described apparatus. The capillary was spun at a speed of about 1483 rpm for about 15 minutes.

A mixture of chemical species was prepared in a mobile phase comprising an 80:20 solution of Acetonitrile:4 mM borate, having a pH of 9. The separation was performed at an applied voltage of 20 kV, resulting in a current of 0.78 micro-amps. The peaks were identified by spiking, column efficiency was calculated and set out in TABLE 1.

Figure 9:
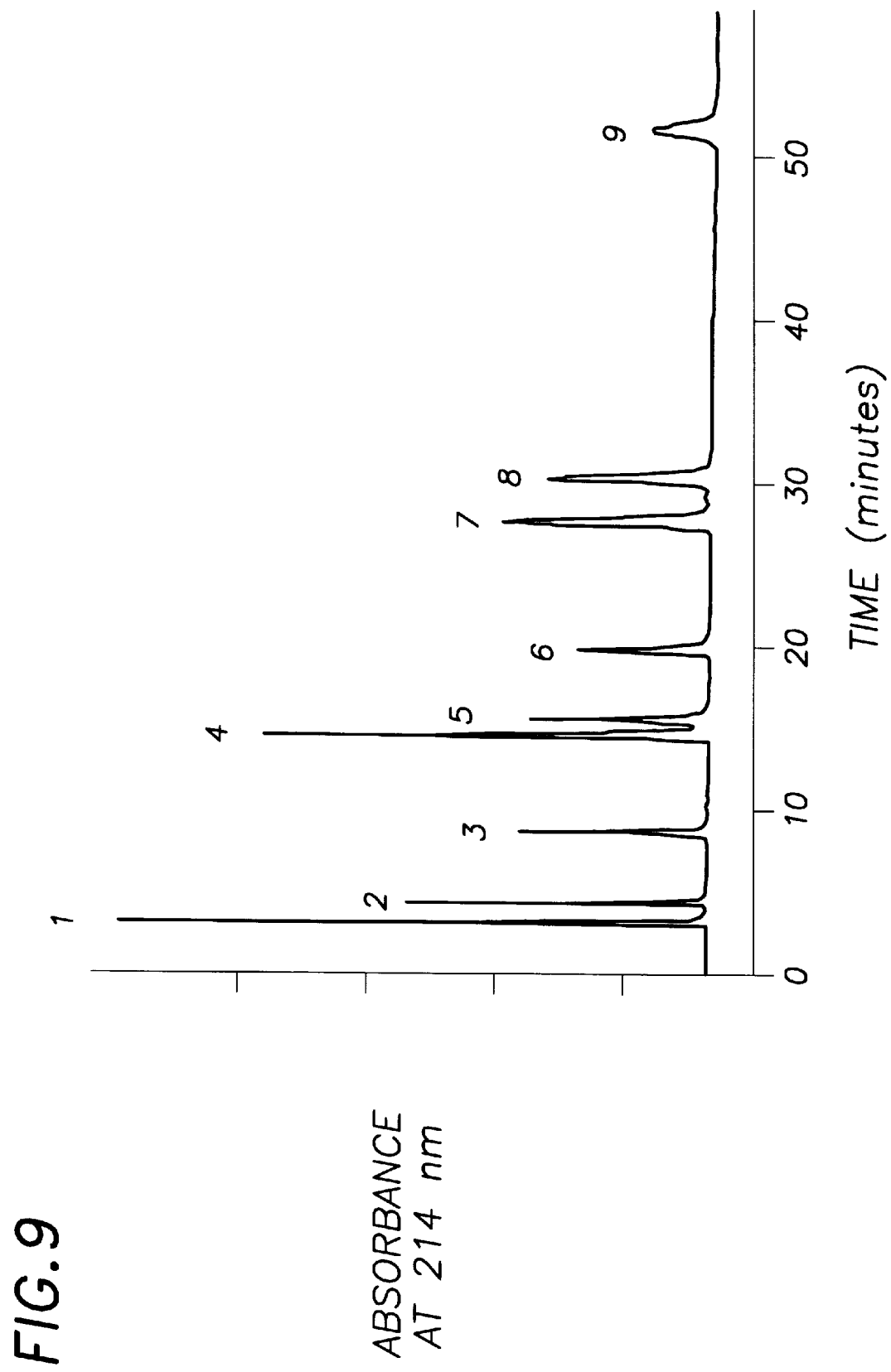
FIG. 9 is a graph depicting species separation in a 250 micron internal diameter capillary column containing a bed packed in accord with the invention.

FIG. 9, comprises a graphic illustration of capillary liquid chromatography species separation in a centripetal packed capillary having an internal diameter of 250 microns, overall length of 33 centimeters and packed bed length of 27 centimeters. The bed was prepared by sonicating a 20 mg/ml slurry of octadesiline (ODS), which is a coated porous particle commonly used in chromatographic separation having an average diameter of 5 microns, in methanol for 10 minutes, and filling the capillary centripetally from a central reservoir in a previously described apparatus. The capillary was spun at a speed of about 2200 rpm for about 15 minutes.

A mixture of chemical species was prepared in a mobile phase comprising a 60:40 solution of Acetonitrile: distilled water. The separation was performed by capillary liquid chromatography, at a flow rate of 1.5 $\mu$L/min, with sample injection of 60 nL of (1) thiourea, (2) benzylalcohol, (3) benzene, (4) toluene, (5) ethylbenzene, (6) biphenyl, (7) ethylnaphthalene, (8) dimethylnaphthalene, and (9) amylbenzene.

While various particular embodiments of the invention have been shown and described, it will, of course be understood that various modifications can be made without departure from the principles of the invention.

TABLE 1

| PEAK | IDENTIFICATION | EFFICIENCY |
| --- | --- | --- |
| 1 | Thiourea | 192,063 |
| 2 | Benzylalcohol | 201,462 |
| 3 | Benzene | N/A |
| 4 | Ethylbenzene | 200,808 |
| 5 | Biphenyl | 222,080 |
| 6 | Ethylnaphthalene | 222,807 |
| 7 | Dimethylnaphthalene | 213,080 |
| 8 | Amylbenzene | 231,411 |

We claim:

1. An apparatus for simultaneously packing a plurality of hollow capillary columns to form active particulate beds therein comprising:

a reservoir, having a chamber arranged for the storage of a slurry around a central axis, said chamber comprising a generally circular inner surface having a plurality of generally equidistant spaced openings therethrough, said openings arranged to enable passage of said slurry radially from said chamber;

means for rotating said chamber about said central axis;

a plurality of elongate hollow capillary columns having openings at opposite ends, the hollow of said columns having an internal diameter less than about 500 microns and comprising a restriction, distal spaced from a first end, the opening formed by said restriction being smaller than the opening of said first end;

means for removably mounting said first ends of said elongate hollow capillary columns to said reservoir, said openings to the first end of said columns being aligned with a corresponding passageway from an opening along the inner surface of the chamber so as to enable the passage of slurry from said opening of said chamber into said hollow column, wherein said mounted column is mounted to extend radially about said central axis and rotate around said central axis in conjunction with rotation of said chamber.

2. The apparatus of claim 1 wherein said column is an elongate chromatographic column and said particulate bed is a chromatographic bed.

3. The apparatus of claim 1 wherein said elongate column is mounted to enable rotation at an angle to said central axis.

4. The apparatus of claim 3 wherein said elongate column is mounted to enable rotation about perpendicular to said central axis.

5. The apparatus of claim 1 wherein said column has an internal diameter of less than about 75 microns.

6. The apparatus of claim 1 wherein said inner surface of said chamber comprises a rounded interior wall angled from the central axis toward said opening for passage of slurry from said chamber.

7. The apparatus of claim 1 comprising means for churning slurry in the chamber during rotation of said chamber.

8. The apparatus of claim 7 wherein said means for churning comprises a wiper arranged to resist rotational movement of said slurry about said central axis during rotation of said chamber.

9. The apparatus of claim 1 wherein said plurality of spaced openings of said chamber are of greater diameter than said openings to said first end of said hollow columns, and said means for mounting comprises a funnel shaped passageway enabled for the passage of said slurry from an opening of said chamber to a first end opening of a hollow column.

10. The apparatus of claim 9 comprising a conical funnel member having a first base end and an opposite smaller base end, said smaller base end being sized to mate over the outer surface of said first end of said hollow column.

11. The apparatus of claim 1 wherein the shape of the inner surface of the chamber is selected from spherical, elliptical and frustoconical.

12. An apparatus for packing a plurality of elongate hollow capillary chromatographic columns with particulate matter to form packed chromatographic beds therein comprising:

a reservoir, having a chamber arranged for the storage of a slurry around a central axis, said chamber comprising a generally circular inner surface having a plurality of generally equidistant spaced openings arranged therethrough to enable passage of said slurry radially from said chamber;

motor means, arranged for rotating said chamber about said central axis;

a plurality of elongate hollow capillary chromatographic columns having openings at first and second ends, the hollow of said columns having an internal diameter less than about 500 microns and comprising a restriction, distally spaced from said first end, suitable for resisting the flow therethrough of particulate matter of a defined size less than about 40 microns;

means for removably mounting said plurality of elongate hollow capillary columns to said reservoir, said means being arranged to enable the passage of said slurry independently from an opening along the inner surface of said chamber to said opening at said first end of a hollow column and comprising a funnel shaped passageway enabled for the passage of said slurry from said opening along said inner surface of said chamber to said opening of said hollow column;

wherein said mounted columns are mounted to extend radially about said central axis and rotate around said central axis in conjunction with rotation of said chamber.

13. The apparatus of claim 12 wherein said restriction comprises a fritted passageway proximate said second opening.

14. A method of simultaneously packing a plurality of elongate hollow capillary chromatographic columns with particulate matter to form packed chromatographic beds therein comprising:

providing a reservoir, having a chamber arranged for the storage of a slurry, said chamber having an inner surface which is about concentric to a central working axis, said inner surface comprising a plurality of spaced, generally equidistant, openings, arranged to enable passage of said slurry radially outwardly from said chamber;

providing means, arranged for rotating said chamber on said central working axis;

providing a plurality of elongate hollow capillary chromatographic columns having openings at first and second ends, the hollow of said columns having an internal diameter less than about 500 microns and comprising a restriction, spaced distal from said first end, arranged to prevent the flow of particulate matter of a defined average diameter not greater than about 40 microns therethrough;

removably mounting said first ends of said plurality of elongate hollow capillary columns in discrete fluid communication with an opening in said chamber, with fluid flow being through a funnel shaped passageway, said columns being arranged radially about said central working axis;

providing a slurry comprising a liquid containing particulate matter having an average particle diameter greater than said defined average diameter, to said chamber of said reservoir;

rotating said reservoir around said central working axis at a speed sufficient to cause said particulate matter comprised in said slurry to pass through said openings in the periphery of said chamber through said funnel shaped passageways into the hollow of said columns; and recovering a plurality of individual columns having a packed chromatographic bed, sized to a packed diameter of less than about 500 microns, of active particulate matter of said defined average diameter.

15. The method of claim 1 wherein said working axis is arranged about perpendicular to a longitudinal axis of said column.

16. The method of claim 14 wherein said column has an internal diameter of less than about 75 microns.

17. The method of claim 14 wherein said means for restricting the passage of particles comprises a fritted passageway at about said second end.

18. The method of claim 14 wherein a plurality of hollow columns are arranged as radial spokes around said working axis.

19. The method of claim 14 wherein said particles have an average particle size of 10 microns or less.

20. The method of claim 14 wherein said particles have an average particle size of from about 0.05 to about 15 microns.

21. The method of claim 14 wherein said chamber comprises a rounded interior wall angled from the central axis toward said opening for passage of particulate matter from said chamber.

22. The method of claim 21 comprising means for churning slurry in the chamber during rotation of said chamber.

23. The method of claim 22 wherein said means for churning comprises a wiper arranged to resist rotational movement of said slurry about said central axis during rotation of said chamber.

24. The method of claim 14 wherein said plurality of openings in said perimeter wall of said chamber is of greater diameter than said first opening of said hollow column, and said means for mounting comprises a funnel shaped passageway enabled for the passage of said slurry from said opening of said chamber to said first opening of said hollow column.

25. The method of claim 24 comprising a conical funnel member having a first base end and an opposite smaller base end, said smaller base end being sized to mate over the outer surfaces of said hollow columns.

26. The method of claim 14 wherein the shape of the inner surface of the chamber is selected from spherical, elliptical and frustoconical.

* * * * *